(12) United States Patent
Koelblin et al.

(10) Patent No.: US 6,337,739 B1
(45) Date of Patent: Jan. 8, 2002

(54) METHOD AND DEVICE FOR QUANTITATIVE AND QUALITATIVE ON-LINE DIFFERENTIATION OF BIOTIC AND ABIOTIC PARTICLES

(75) Inventors: Ruediger Koelblin, Stuttgart; Ralf Grimme, Pleidelsheim, both of (DE)

(73) Assignee: Fraunhofer-Gesellschaft zur Foerderung der Angewandten Forschung E.V. (DE)

(*) Notice: Subject to any disclaimer, the term of this patent is extended or adjusted under 35 U.S.C. 154(b) by 0 days.

(21) Appl. No.: 09/403,346

(22) PCT Filed: Apr. 16, 1998

(86) PCT No.: PCT/EP98/02239

§ 371 Date: Dec. 14, 1999

§ 102(e) Date: Dec. 14, 1999

(87) PCT Pub. No.: WO98/48259

PCT Pub. Date: Oct. 29, 1998

(30) Foreign Application Priority Data

Apr. 21, 1997 (DE) .......................... 197 17 749

(51) Int. Cl.$^7$ .............................. G01N 15/02
(52) U.S. Cl. ...................... 356/336; 356/437
(58) Field of Search .................. 356/335, 336, 356/339, 341, 342, 343, 437, 432; 422/95, 80, 78, 83; 73/28.01, 61.77; 702/25, 28

(56) References Cited

U.S. PATENT DOCUMENTS

| | | |
|---|---|---|
| 4,541,719 A | 9/1985 | Wyatt |
| 4,605,535 A | 8/1986 | Dimpfl |
| 4,670,137 A | 6/1987 | Koseki et al. |
| 5,090,233 A | 2/1992 | Kogure et al. |
| 5,401,468 A | 3/1995 | Patashnick et al. |

FOREIGN PATENT DOCUMENTS

| | | |
|---|---|---|
| DE | 41 07 902 A1 | 1/1992 |
| JP | 4-304898 A | 10/1992 |
| WO | WO 94/19674 A1 | 9/1994 |

OTHER PUBLICATIONS

Patent Abstracts of Japan; JP 04–304898 A; Section C, vol. 17, No. 124 (1993) C–1035.

*Primary Examiner*—Frank G. Font
*Assistant Examiner*—Tu T. Nguyen
(74) *Attorney, Agent, or Firm*—Marshall & Melhorn, LLC (57) ABSTRACT

The invention relates to a method and a device for quantitative and qualitative on-line differentiation of biotic and abiotic particles. The methods and devices are used to ensure quality and to monitor production as well as in analysis procedures for particular contamination's of gaseous media. The methods and devices are chiefly used in pharmacology, food technology, medicine, biotechnology and health care and in controlling maximum admissible concentration values. According to the inventive method, the gas sample to be measured is briefly heated at very high temperatures in a heating chamber (3). Dimensional distribution of particle contamination is determined before and after heating by means of diffuse light sensors (1, 2). Dimensional changes of biotic panicles caused by heating make it possible to determine their proportion in total particle load of the gas sample and their composition.

14 Claims, 10 Drawing Sheets

FIG. 1

| PURITY CLASSIFI-CATION | COMMENT | MAXIMUM PERMISSIBLE NUMBER OF PARTICLES PER m³ | | MAXIMUM PERMISSIBLE NUMBER OF AIR-BORNE PARTICLES PER m³ |
|---|---|---|---|---|
| | | >0.5um | >5um | |
| A | LAMINAR AIRFLOW | 3,500 | 0 | <1 |
| B | TURBULENT AIRFLOW | 3,500 | 0 | 5 |
| C | TURBULENT AIRFLOW | 350,000 | 2,000 | 100 |
| D | TURBULENT AIRFLOW | 3,500,000 | 20,000 | 500 |

METHOD AND DEVICE FOR QUANTITATIVE AND QUALITATIVE ON-LINE DIFFERENTIATION OF BIOTIC AND ABIOTIC PARTICLES

BACKGROUND OF THE INVENTION

1. Field of the Invention

The invention relates to a method and a device for quantitative and qualitative on-line differentiation of biotic and abiotic particles.

Methods and devices of this kind are used to ensure quality and to monitor production as well as in analysis procedures for particle contamination in gaseous media. They are used especially in pharmacology, food technology, medicine, bio-technology, in health care, and for monitoring maximum admissible concentration values.

In these spheres, biotic particle contamination, in particular living particle contamination such as airborne germs for example, in gaseous media such as for example ambient air or an inert gas atmosphere, plays a special role for the quality of the produce or for the safety of the production staff or the end consumer, and for this reason monitoring the purity of these gaseous media is an absolute necessity and is in most cases prescribed as obligatory by law.

Figure 1:
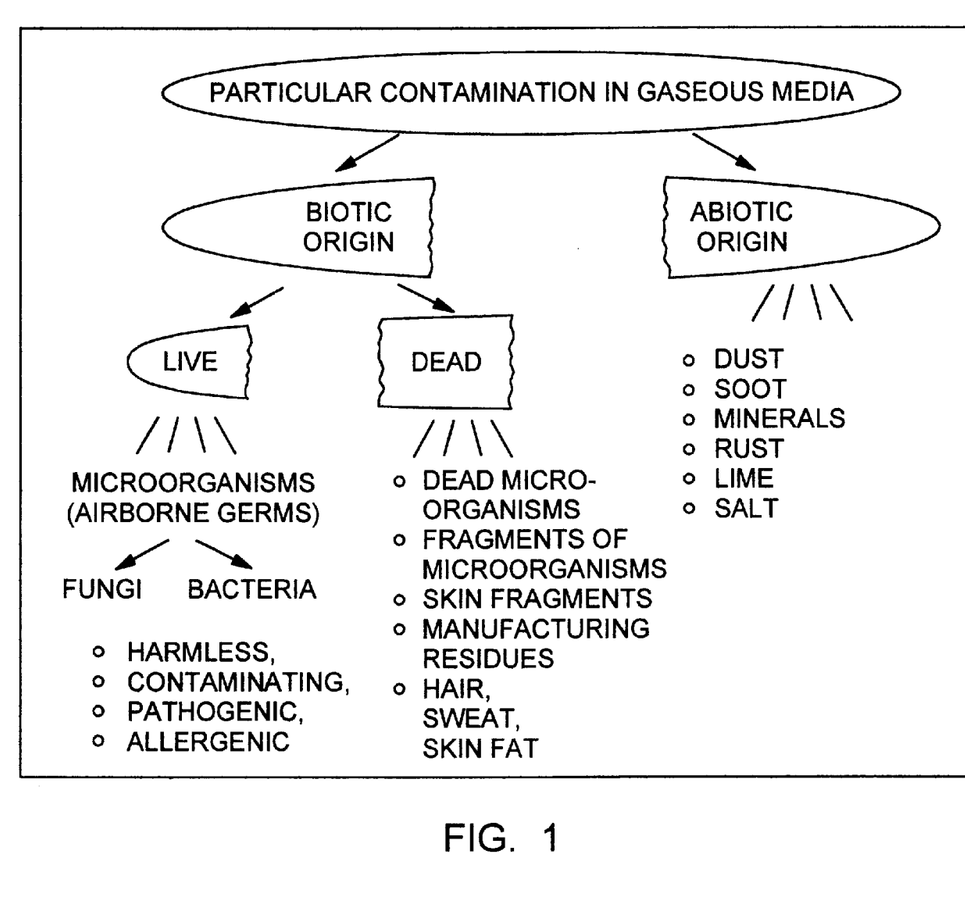

FIG. 1 shows the basic division of the particle contamination in gaseous media into particles of biotic origin and of abiotic origin. The particles of biotic origin can be further sub-divided into living or already dead particles. As dead particles occur especially dead micro-organisms or fragments thereof, pieces of skin, production residues and hair, sweat or skin grease. The still living particles of biotic origin consist for the greater part of micro-organisms such as fungi or bacteria (airborne germs) or also of germs or spores from plants.

Figure 2:
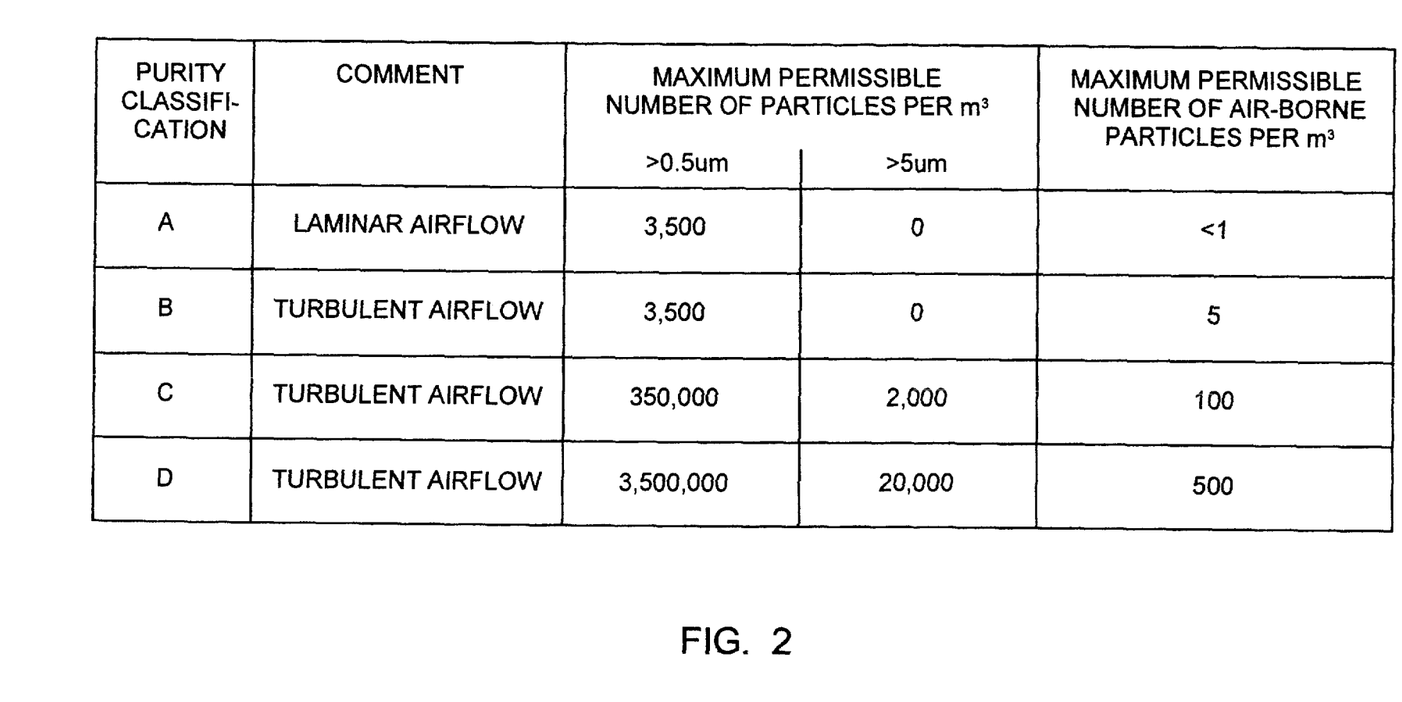

Within sterile production systems, the particularly strict limit values for particles of biotic origin, as prescribed by the Federal Drug Administration, by the Good Manufacturing Practices Guideline or by Sheet 3 of the VDI—Richtlinie 2083, have to be observed. These limit values are shown in FIG. 2. Furthermore, the methods for determining air bacterial counts are prescribed by these guidelines.

The following methods describe the state of the art for determining living particle contamination in gaseous media.

Sedimentation

In this method, agar plates are laid out open in the atmosphere to be measured. Then the precipitated micro-organisms are determined. Specifying can be achieved through the use of selective culture media.

Filtration

In this method, the germs or germ formations contained in a volume of gas, are deposited on a filter through which the gas flows. The filters are then applied directly to a suitable culture medium. Alternatively, the filter membrane can be dissolved in a sterile physiological nutritive solution, and this can then be filtered. The material of the membrane is mostly gelatine or cellulose ester. This quantitative measuring procedure is used in particular with very high bacterial counts or in simultaneous checking of the germs on different selective culture media.

Inertial Separation

In this group of methods, the germs are deposited in different materials, for example in liquids or on solid culture media. An example of this type of method is the deposition of germs by means of glass impact separators. This method works according to the Bubbler principle, in which the air to be measured is led through a liquid at a high flow rate. The airborne bacteria are retained in the liquid and the remainder of the air escapes in the form of bubbles. Because of the high air speeds, anti-foaming agents must be added to the liquid. In order to avoid any undesired increase in airborne bacteria in the liquid, rapid further processing is unavoidable.

With deposition on solid culture media, a distinction is made between centrifugal collectors, sieve collectors, slit collectors or electro-precipitation. With the centrifugal collectors, a definite volume of air is set in rotation through suitable flow guiding. The particles located in the volume of air, are hurled onto an agar strip, which is situated on the cylindrical wall of the measuring device. Then the agar strip is incubated and counted as usual. The sieve collector works according to the principle of the multi-stage impactor. The sample volume is sucked in through a system of several series-connected sieve plates. The hole diameter of the individual sieve plates decreases in the direction of the flow guiding and parallel to the decreasing hole diameters. The airborne particles are deposited as a result of their inertia and of the flow which becomes ever faster, independently of their size, on different sieve plates. Thus there is separation of the particles according to their size. In the slit collector, the sample volume is sucked in through a slit and hurled at high speed onto a rotating culture medium plate. In electro-precipitation, the sample volume is led directed through a high-voltage field. The electrostatic forces here ensure deposition of charged particles onto a rotating inversely and oppositely charged surface. This surface generally consists of a solid culture medium which is then incubated and counted.

On all the methods mentioned, the air particles have to be caught, for example by laying out petri dishes with solid culture media, and then incubated. This process can last up to five days. Thereafter the incubated cultures are described exactly and there is detailed evaluation of the contamination load of the air at the time of taking the sample. Tracing back directly the possible causes for the contamination is mostly no longer possible because of the time delay. The products produced and contaminated in the meantime must in the worst case be completely disposed of. What is disadvantageous about the above-mentioned methods is, therefore, that the sampling has to be prepared in a very expensive manner, that the sample then has to be subjected to a plurality of method steps, whereby the risk of contamination during the evaluation process is greatly increased, and that the evaluation can only take place after a certain incubation time of the cultures, on average 3 to 5 days. For this reason, mostly also no qualitative measurement is possible, particularly as the quality of the measurements depends greatly on the behaviour of the operating personnel. These methods therefore assume highly-qualified personnel and may only be slightly automated.

2. Description of the Related Art

JP-A 04 304898 discloses a method of determining microorganisms in gaseous or liquid media, in which the refractive index of the particles of biotic origin may be altered with the aid of heat treatment. On the basis of measurement of the refractive index both before and after this heat treatment, the number of the particles of biotic origin can then be determined. For this heat treatment, the medium is heated up for one to ten minutes to 400° to 80° C. and then cooled again. Optimum operating parameters emerge with heating for one to two minutes to 70° C. In the result, the protein of the particles of biotic origin is de-natured by this treatment and the refractive index is thereby altered. According to JP-A-04-304898, during this heat treatment the size of the particles of biotic origin does not alter significantly and can therefore not be used to differentiate between particles of biotic and abiotic origin. Another disadvantage of this method is the fact that the duration of the measurements is in the ten minute range and thus admittedly relatively short compared with the above depicted methods of prior art. However, the period of heating ranging from one to ten minutes and the subsequent cooling prevent its use as a genuine on-line measuring method. On the basis of the still lengthy heating time, only a batch method can be realised.

OBJECT OF THE INVENTION

The object of the present invention is to create a method and a device for quantitative and qualitative on-line differentiation of biotic and abiotic particles in a gaseous medium, which has very short reaction times for genuine on-line measurement, high reproducibility of the measuring results, and renders possible a high degree of automation and simple handling.

This object is achieved by determining the number and size of particles in the gaseous medium in a first measuring device, heating the gaseous medium to temperatures above 100° C., determining the number and size of particles in the heated gaseous medium in a second measuring device, and determining the number and/or size of the biotic and abiotic particles present in the gaseous medium from the first and second determinations. This is best carried out in a device comprising first and second scattered light particle counters, each having an intake and an outlet for gaseous media. The outlet of the first light particle counter goes through a heater, into the inlet of the second particle counter.

The achievement of the object according to the invention rests on a deliberate combination of determining the number and size of the particles present in a medium, with the alteration of particles of biotic origin through brief heating to high temperatures which lie above 100° C. As a result of the high temperatures, only very short heating periods are necessary in the region of fractions of seconds to a few seconds. Through this heating, the particles of biotic origin shrink, for example through release of water or also, with less significance, denaturing of the proteins, and the size distribution of the particles in the medium is noticeably altered. Through evaluation of these changes it is possible directly to determine within seconds the proportion of particles of biotic origin in the total particle load of the medium.

The method according to the invention may therefore be carried out continuously and is completely possible in real time and does not represent any batch method as in prior art even if apparently carried out continuously. The reaction times for the operating personnel to alteration in the particle composition of the medium are drastically reduced and the measuring results are very reproducible. The efficiency of the detection of the airborne bacteria is also very high as a result of the high temperatures used.

The method according to the invention and the device according to the invention, which manages with very few components, render possible a modular, compact apparatus structure, high apparatus safety and therefore low plant costs as well as low operating and maintenance costs. The degree of automation of this genuinely continuous on-line measurement is very high and therefore simple handling of the method even by personnel who have not been specially trained is possible.

Figure 7A:
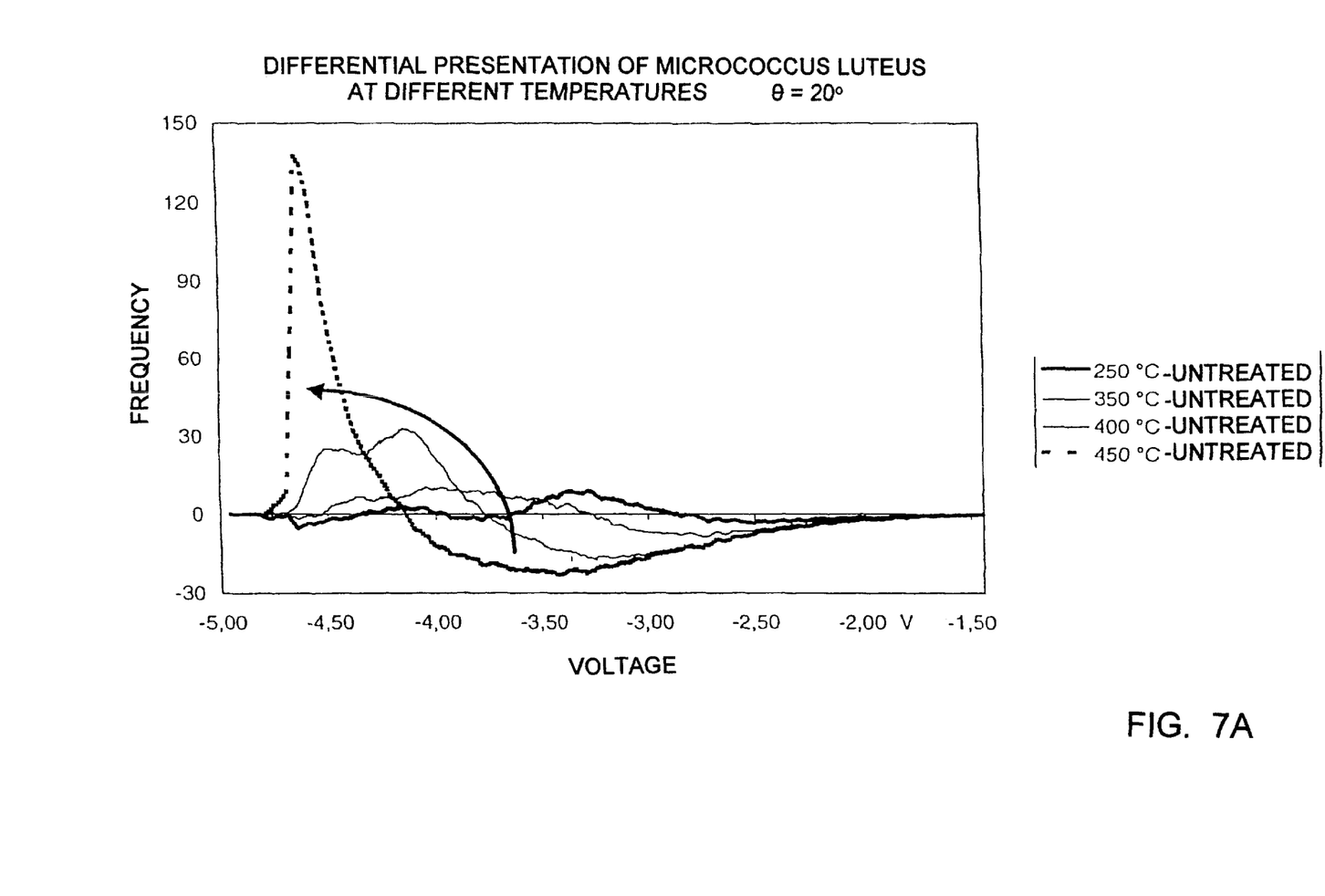
Figure 7B:
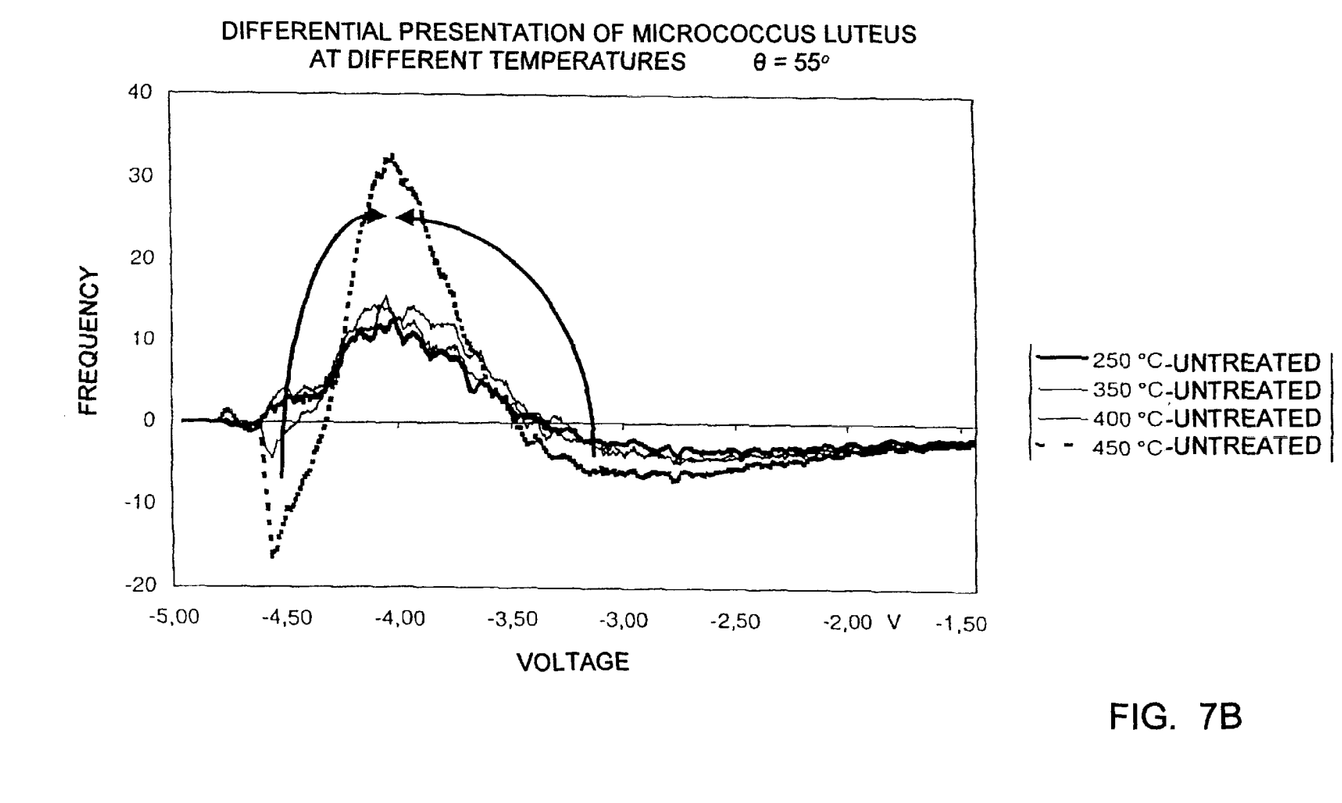
Figure 7C:
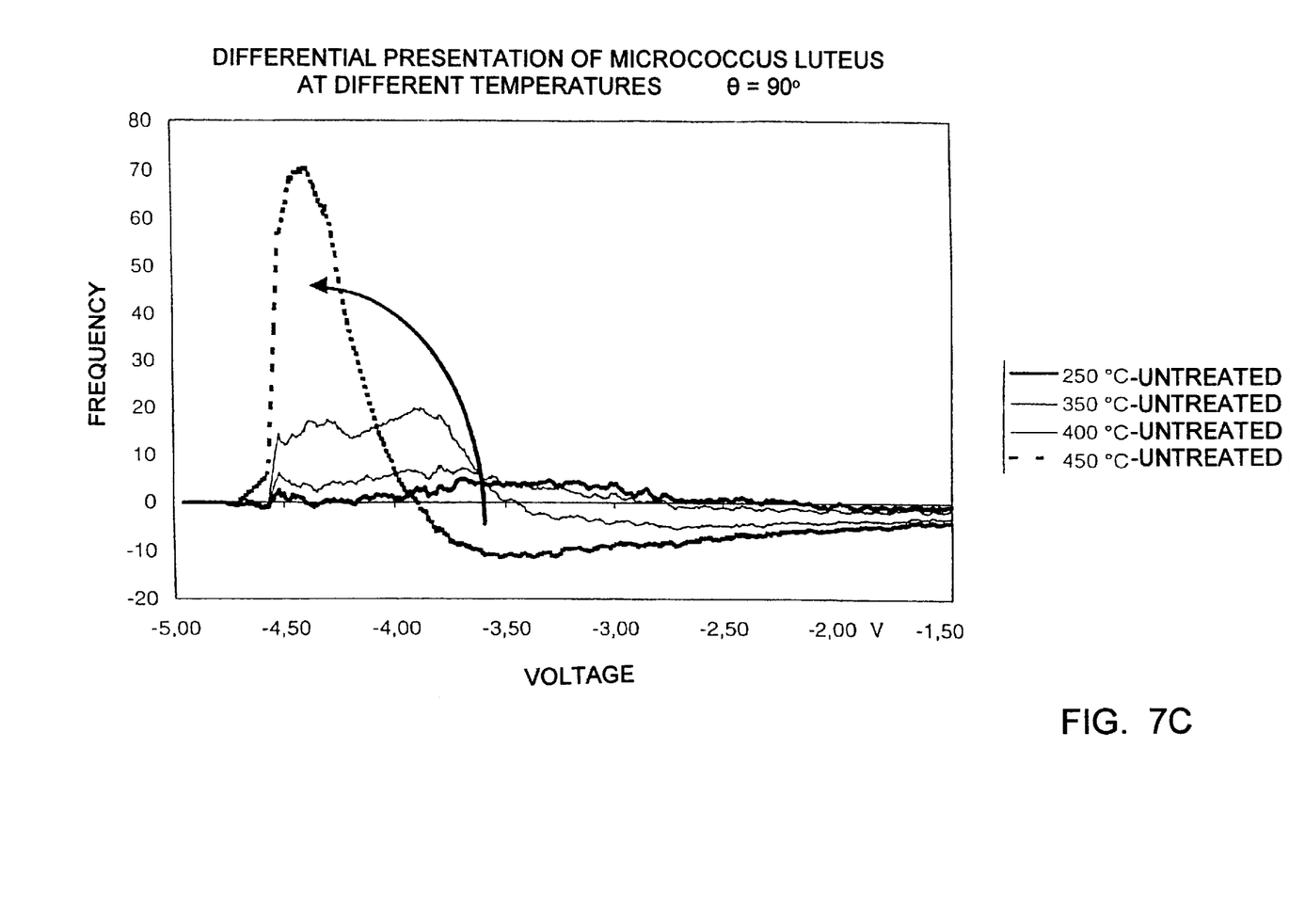
Figure 8:
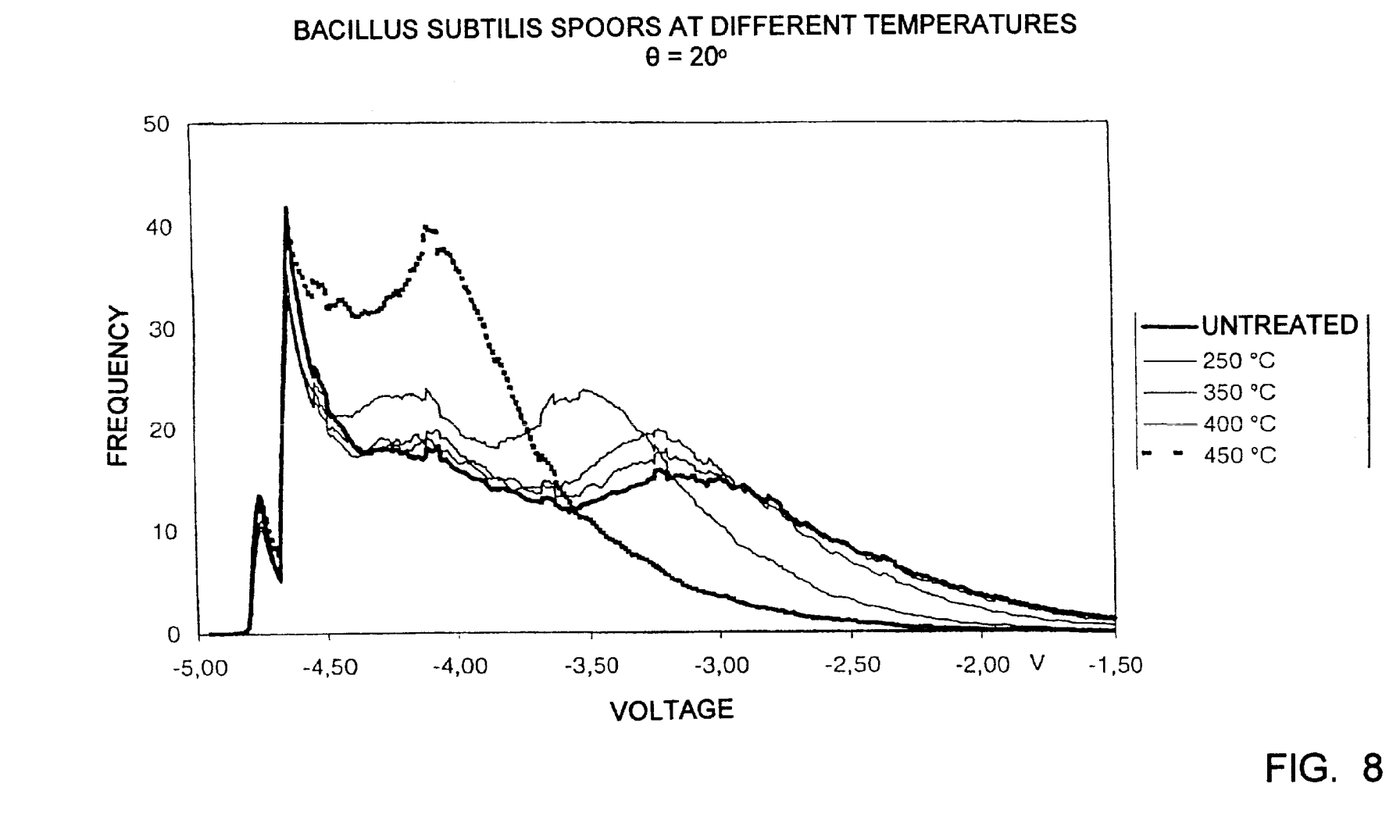

The invention renders possible quick reaction to negative changes in relation to particle contamination of biotic origin within gaseous media, such that effective monitoring of production and quality assurance are possible. Differentiation of the type of contamination within the individual contamination groups (biotic origin or abiotic origin) is also possible with this method. It is immediately clear that, as a result of the different water content of the particles of biotic origin, for example micro-organisms with high water content or plant spores with extremely low water content, the temperature and the duration of heating the sample has to be adapted according to the particles to be determined. The exact conditions to be observed can however be determined by a simple series of experiments.

Advantageous developments of the method according to the invention and of the device according to the invention are given in the dependent claims.

A particularly short heating period and a particularly strong alteration in the size of the particles of biotic origin arise at temperatures above 200° C. or better still 400° C., and particularly advantageously above 450° C. Many particles of biotic origin alter their size only after being heated for a few seconds at temperatures above 200 or 400° C. Short high temperature heating times of this type can be achieved through the use of a test tube with a small diameter, for example a capillary, as the heating chamber.

In addition to the change in the size of the particles of biotic origin, alterations of additional physical particle parameters can also be determined, for example the refractive index or the surface structure of the particles of biotic origin before and after heating, and used in addition to differentiate and evaluate the measurement results. With this information, differentiation within the particles of biotic origin can also be further improved. Scattered light methods are particularly suitable here as measuring methods for determining the size of the particles, the use of a multi-angle scattered light detection making possible complete description and high reliability in determining these characteristics.

The heating of the sample can advantageously come about with the aid of a heat exchanger, for example through heating up the thin tube described above or the thin capillary described above.

BRIEF DESCRIPTION OF THE DRAWINGS

A few examples of the method according to the invent on and the device according to the invention are described below.

FIG. 1 Shows the differentiation of the particle contamination in gaseous media, FIG. 2 shows the limit values to be observed for particle contamination in gaseous media, according to various guidelines, FIG. 3 shows the structure of a device according to the invention as well as its measurement principle, FIG. 4 shows the structure of a multi-angle detector according to the invention, FIG. 5A, shows the frequency at which particles at a given diameter occur in the non-heated sample, FIG. 5B shows the corresponding frequency distribution of the particle sizes of the same gas sample after heating, FIG. 5C shows the difference between the frequency distributions of FIGS. 5A and 5B, FIG. 6 shows measuring results according to the method of the invention, FIG. 7A shows the alteration of the size distributions of *microccus luteus* microorganisms through heating at different temperatures, at a scattering angle of 20°, FIG. 7B shows the alteration of the size distributions of *microccus luteus* microorganisms through heating at different temperatures, at a scattering angle of 55°, FIG. 7C shows the alteration of the size distributions of *microccus luteus* microorganisms through heating at different temperatures, at a scattering angle of 90°, FIG. 8 shows further measuring results according to the method of the invention.

DESCRIPTION OF THE PREFERRED EMBODIMENTS

FIGS. 1 and 2 have already been described above and reproduce the biological bases of particle differentiation as well as the legal limit values for particle contamination in air.

Figure 3:
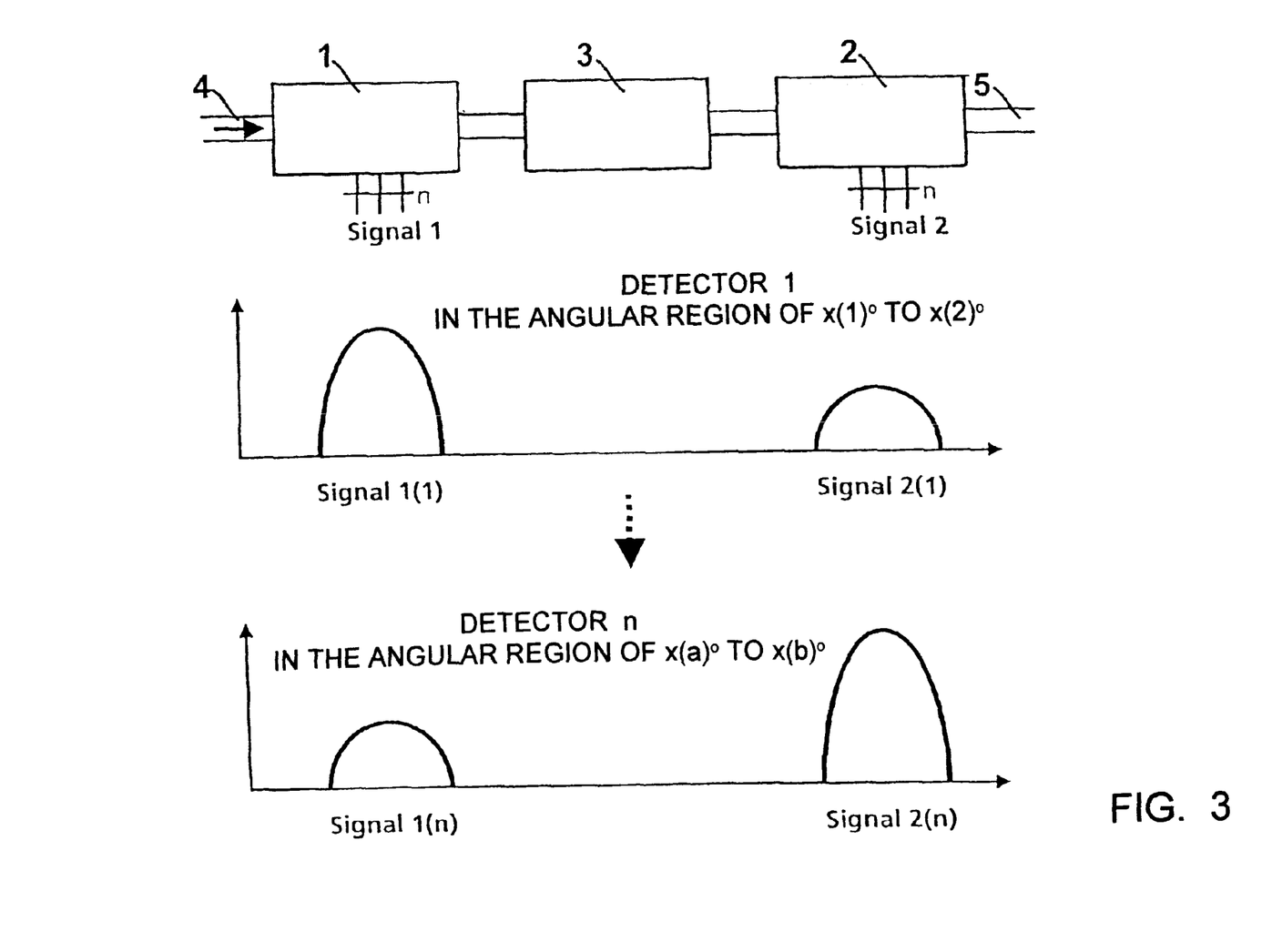
Figure 4:
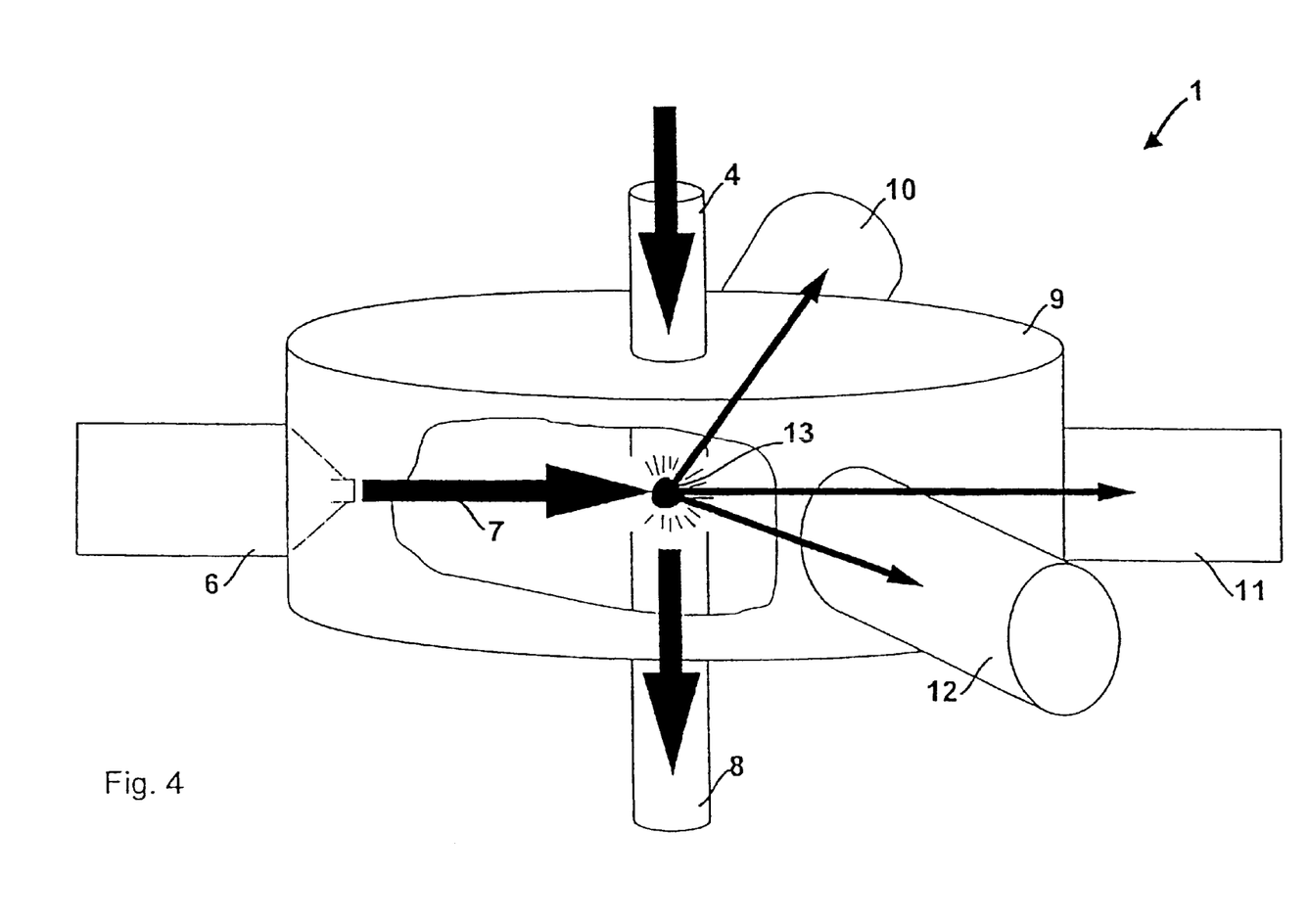
Figure 5A:
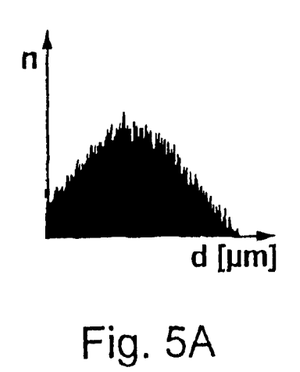
Figure 5B:
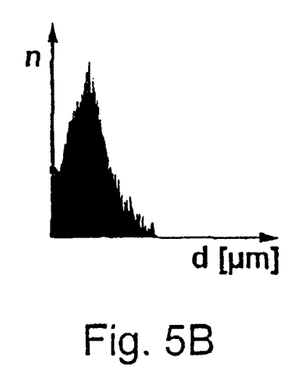
Figure 5C:
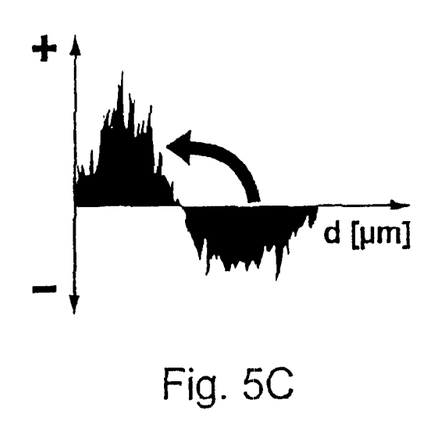
Figure 6:
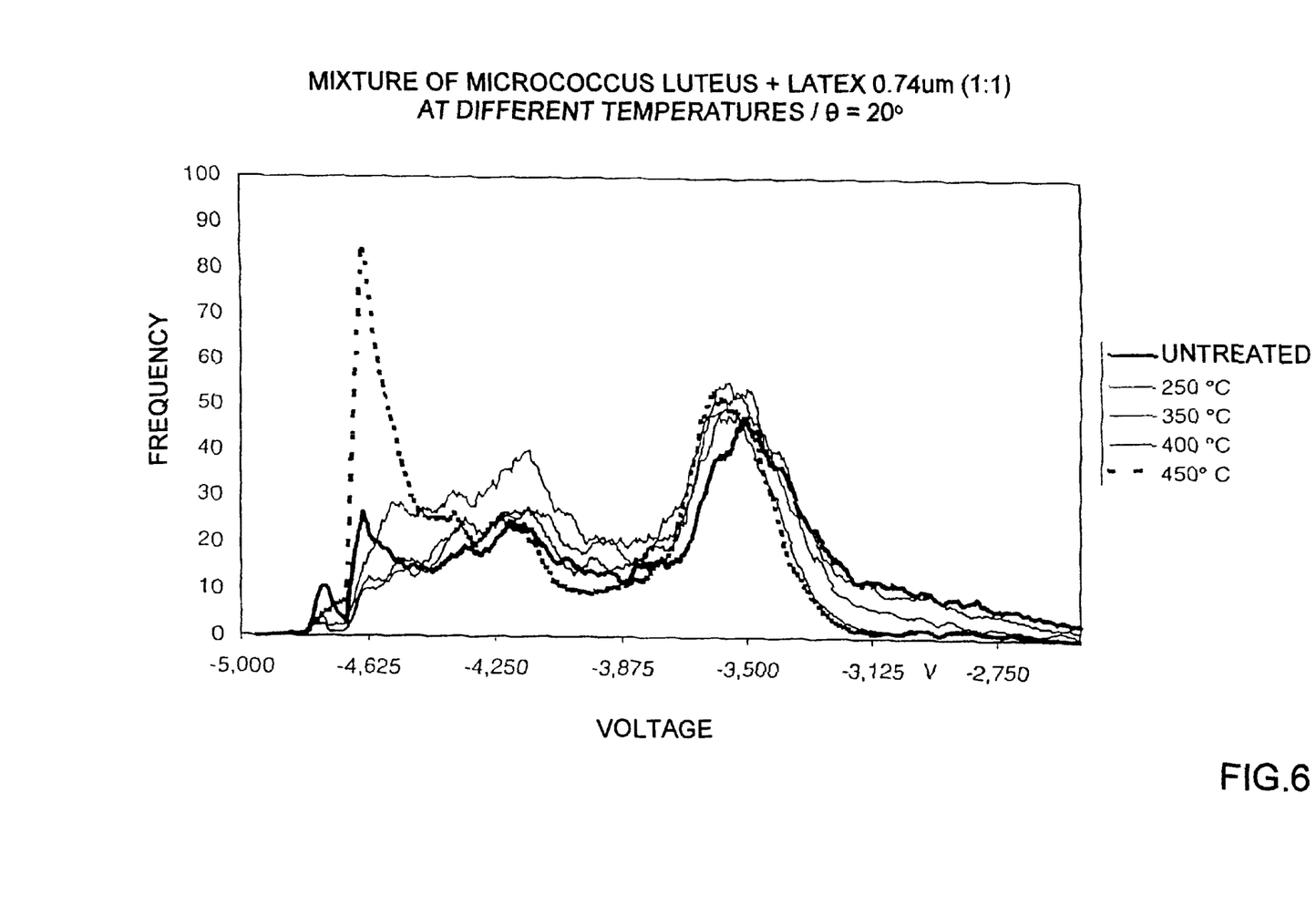

FIG. 3 shows a device according to the invention which has two scattering angle detectors 1 and 2 as well as a heating chamber 3 for heating up the sample. The sample, of which the concentration of particles of biotic origin is to be measured, is led through an intake 4 into the first scattering angle detector 1.

There angle-dependent first signals of physical properties (such as for example size, refraction) of the particles contained in the medium are generated. Then the gaseous medium is heated up in the heating chamber 3 and then measured again in the scattering angle detector 2 and further signals 2 emitted. After this measurement the gaseous media is blown via the outlet 5 of the scattering angle detector 2 out of the measuring device according to the invention. The two diagrams in FIG. 3 show the measurement signals in dependence on the detector voltage. This corresponds to the size distribution of the particles in the sample. FIG. 3 now shows how the size distribution alters as a result of heating the gas in the heating chamber 3. Here the two diagrams represent the signals of the scattering angle detectors 1 and 2 at different scattering angles. Thus simultaneously is shown that the signal and its alteration naturally depends on the angle at which the scattered light is observed. Furthermore, the scattering naturally also depends on the measuring light radiated onto the gaseous medium to generate the scattering of the diffuse light.

FIG. 4 shows a multi-angle scattered light detector 1, according to the invention, with a gas intake 4, a gas outlet 8 and three individual scattered light detectors 10, 11 and 12, which are disposed along the circumference of a measuring chamber 9. The multi-angle scattered light detector 1, according to the invention, has in addition a laser light source 6, which generates a laser beam 7. The laser beam 7 impinges at a measuring location 13 on the gas flow streaming from the intake 4 to the outlet 8 and generates there scattered light which is detected at three different angles, which are indicated by arrows, by the three detectors 10, 11 and 12. With the aid of these differing detection angles, material-independent (bending) and material-dependent (refraction, reflection) physical properties can be detected in parallel. Through the use of a multi-angle detector of this type, which simultaneously receives the scattered light signal in a plurality of different angles suitable for recognising individual physical effects, thus a differentiated statement about the achieved changes not only in size but also for example in the surface or the refractive index can be made. In the method according to the invention, however, the alteration of the size of the particles generated by heating plays the essential role.

Through the use of two constructionally alike multi-angle scattered light detectors to determine the size of the particles before or after heating to high temperatures, a differential measurement is realised and distinguishing between contamination of biotic and abiotic origin is rendered possible. The result of the differential measurement produces a statement about the respective number of particles of biotic and abiotic origin in the gas sample to be measured. The cause of this is to be found in the fact that particle contamination of abiotic origin does not show any dependence of size distribution on heating. For this reason differences in measurements before or after heating the gas sample are a measure for particle contamination of biological origin and thus render possible the exact determination of the number of particles of biotic origin in the gas sample and thus a direct conclusion about the loading of the medium for example with airborne bacteria.

FIG. 5 shows as a model the change in the particle size distribution through heating of a gas sample to 450° C. for a few seconds. FIG. 5A shows the frequency n at which particles with a diameter d occur in the non-heated sample, i.e. in detector 1. FIG. 5B shows the corresponding frequency distribution of the particle sizes of the same gas sample in detector 2, i.e. after heating of the sample volume. FIG. 5C shows the difference between the two described frequency distributions. It can be easily seen that the size of the particles of biotic origin has reduced as a result of the heating, such that the proportion of smaller particles has increased and the proportion of larger particles has decreased. From this change it is possible to infer in a simple manner the total number of particles of biotic origin in the original air sample.

FIG. 6 shows the dependence of the size change in the particles of biotic origin on the heating temperature. For these measurements, a mixture of *micrococus luteus* and latex particles with a diameter of 0.74 μm, mixed in a ratio of 1:1, were heated at different temperatures. The diagram presented shows the scattered light signal at a scattering angle of 20° in dependence on the detector voltage. This corresponds to the above depicted frequency distribution of the particle sizes. It can be seen immediately that only when heated above 400° C. does the size of the *micrococus luteus* organisms reduce drastically. Only at these high heating temperatures does the large volume particle proportion detected at a low negative detector voltage, reduce significantly and there is then a steep frequency peak at high detector voltages, i.e. with small particle sizes. This peak, occurring at high temperatures above 400° C., corresponds to the *micrococus luteus* micro-organisms which have shrunk severely as a result of heating, whilst the latex particles have not experienced any alteration in their size through heating. This temperature behaviour also confirms that the changes in the scattered light signal essentially do not reflect alterations of the refractive index as a result of denaturing of the proteins of the particles of biotic origin, since in this case a signal change would be expected from approximately 60° C. already.

FIG. 7 shows the alteration of the size distributions of *micrococus luteus* micro-organisms through heating at different temperatures. Here FIG. 7A is recorded at a scattering angle of 20°, FIG. 7B at a scattering angle of 55° and FIG. 7C at a scattering angle of 90°. It can be seen immediately that the observed signal alterations depend on the angle of observation. Furthermore it can be taken from all three curves 7A to 7C, that only at temperatures of above 450° C. does a noticeable change occur in the signal. A clear change in the signal which is excellently suitable for evaluation, only occurs at temperatures around 450° C.

FIG. 8 shows a further example, at which the scattered light signal of *bazillus subtilis* spores was measured at an angle of 20° after heating to various temperatures. Although *bazillus subtilis* spores have a very low water content, at heating up to 400° C. or, better still, to 450° C., a noticeable alteration in the scattered light signal, i.e. in the size distribution of the particles can be observed.

In summary, it can be established that with the present invention, a method and a device are made available in which the concentration of particles of biotic origin can be distinguished from the concentration of particles of abiotic origin and the extent to which gaseous media are loaded with particles of biotic origin can be very quickly determined on-line and continuously. This is based essentially on the alteration in size of the particles of biotic origin caused by brief heating to very high temperatures.

What is claimed is:

1. Method of quantitative and qualitative on-line differentiation of biotic and abiotic particles in a gaseous medium, characterised in that, in a first measuring device (1), the number and size of the particles present in the gaseous medium is determined, the gaseous medium is heated for a few seconds to a temperature above 200° C., in a second measuring device (2) the number and size of the particles present in the heated gaseous medium is determined and, from the results of the first and the second determination, the number and/or size of the biotic and abiotic particles present in the gaseous medium is determined.

2. Method according to claim 1, characterised in that the medium is heated for a few seconds to temperatures above 400° C.

3. Method according to claim 1, characterised in that, apart from the size distribution, simultaneously additional physical particle parameters are determined.

4. Method according to claim 3, characterised in that the distribution of the refractive index of the particles is simultaneously determined.

5. Method according to claim 1, characterised in that the method is applied to a continuous stream of gaseous medium.

6. Method according to claim 1, characterised in that, for heating, the gaseous medium is led through a thin heated test tube (3) or capillary.

7. Method according to claim 1, characterised in that the distribution of size and/or of the refractive index of the particles in the gaseous medium is determined by means of a scattered light process.

8. Method according to claim 7, characterized in that the scattered light proceeding from the particles is detected at at least two different angles (multi-angle detection).

9. Device for quantitative and qualitative on-line differentiation of biotic and abiotic particles in a gaseous medium, characterised in that a first and a second scattered light particle counter (1,2), each having an intake (4) and an outlet (5,8) for gaseous media, and a heating chamber (3) are provided, the heating chamber being configured to be intermittently heated above 200° C., the sample outlet of the first scattered light particle counter and the sample intake of the second scattered light particle counter being connected with one another, leading the gaseous medium through the heating chamber (3).

10. Device according to claim 9, characterised in that the scattered light particle counters (1, 2) are multi-angle detectors.

11. Device according to claim 9, characterised in that the heating chamber comprises a thin tube.

12. Device according to claim 9, characterised in that the tube has a temperature above 400° C.

13. Device according to claim 9, characterised in that the tube is a capillary.

14. Device according to claim 9, characterised in that a heat source is arranged on the tube.

* * * * *